(12) United States Patent
Steinbach (10) Patent No.: US 8,876,771 B2
(45) Date of Patent: Nov. 4, 2014

(54) PROPELLANT PILLOW MANUFACTURING TECHNIQUE

(75) Inventor: Bernd Steinbach, Friedberg (DE)

(73) Assignee: Palyon Medical (BVI) Limited (VG)

( * ) Notice: Subject to any disclaimer, the term of this patent is extended or adjusted under 35 U.S.C. 154(b) by 947 days.

(21) Appl. No.: 12/947,187

(22) Filed: Nov. 16, 2010

(65) Prior Publication Data

US 2012/0118428 A1   May 17, 2012

(51) Int. Cl.
*A61M 1/00*  (2006.01)
*A61M 5/155*  (2006.01)
*A61M 5/142*  (2006.01)

(52) U.S. Cl.
CPC ........... *A61M 5/155* (2013.01); *A61M 5/14276* (2013.01)
USPC ........ 604/153; 156/145; 604/93.01; 604/151; 141/166

(58) Field of Classification Search
CPC .. A61M 5/148; A61M 5/155; A61M 5/14276
USPC .............. 141/3, 10, 20, 65, 66, 166; 156/145–147; 604/151, 153, 93.01
See application file for complete search history.

(56) References Cited

U.S. PATENT DOCUMENTS

| | | | | |
|---|---|---|---|---|
| 2,764,862 A * | 10/1956 | Pickering | | 53/374.8 |
| 4,543,769 A * | 10/1985 | Schmitz | | 53/450 |
| 4,817,800 A * | 4/1989 | Williams et al. | | 206/484 |
| 4,969,873 A | 11/1990 | Steinbach et al. | | |
| 5,045,064 A * | 9/1991 | Idriss | | 604/132 |
| 5,085,656 A | 2/1992 | Polaschegg | | |
| 5,336,194 A | 8/1994 | Polaschegg et al. | | |
| 5,722,957 A | 3/1998 | Steinbach | | |
| 5,766,150 A | 6/1998 | Langkau | | |
| 5,814,019 A | 9/1998 | Steinbach et al. | | |
| 5,836,915 A | 11/1998 | Steinbach et al. | | |
| 5,938,877 A * | 8/1999 | Schram | | 156/145 |
| 6,117,465 A * | 9/2000 | Falla | | 426/127 |
| 6,209,286 B1 * | 4/2001 | Perkins et al. | | 53/403 |
| 6,871,759 B2 * | 3/2005 | Rake et al. | | 222/103 |
| 7,083,068 B2 * | 8/2006 | Rake et al. | | 222/103 |
| 7,708,730 B2 * | 5/2010 | Steinbach et al. | | 604/500 |
| 8,231,598 B2 * | 7/2012 | Steinbach et al. | | 604/415 |
| 2002/0112808 A1 * | 8/2002 | Perkins et al. | | 156/145 |
| 2003/0135159 A1 * | 7/2003 | Daily et al. | | 604/141 |
| 2006/0259015 A1 | 11/2006 | Steinbach | | |
| 2006/0259016 A1 | 11/2006 | Steinbach | | |
| 2006/0271021 A1 | 11/2006 | Steinbach | | |
| 2006/0271022 A1 | 11/2006 | Steinbach et al. | | |
| 2007/0005044 A1 | 1/2007 | Steinbach et al. | | |
| 2007/0112328 A1 | 5/2007 | Steinbach et al. | | |
| 2008/0215029 A1 * | 9/2008 | Rake et al. | | 604/408 |
| 2009/0311133 A1 * | 12/2009 | Pang et al. | | 422/22 |
| 2011/0319863 A1 * | 12/2011 | Steinbach et al. | | 604/500 |
| 2012/0136304 A1 * | 5/2012 | Wyss et al. | | 604/151 |
| 2012/0238955 A1 * | 9/2012 | Wyss | | 604/151 |

OTHER PUBLICATIONS

U.S. Appl. No. 12/069,385.

* cited by examiner

*Primary Examiner* — Timothy L Maust (74) *Attorney, Agent, or Firm* — Lerner, David, Littenberg, Krumholz & Mentlik, LLP (57) ABSTRACT

An improved technique for manufacturing a propellant pillow for use in filling a propellant chamber of an implantable pump is disclosed. The method preferably results in the creation of an already filled propellant pillow, which therefore negates the need for the separate filling of the pillow.

16 Claims, 7 Drawing Sheets

FIG. 7B

PROPELLANT PILLOW MANUFACTURING TECHNIQUE

BACKGROUND OF THE INVENTION

The present invention relates to a manufacturing technique for a propellant pillow for use in filling a propellant chamber of an implantable pump, in particular, a technique that produces a filled propellant pillow without the need for a separate filling operation.

Implantable pumps have been well known and widely utilized for many years. Typically, such pumps are implanted into patients who require the delivery of active substances or medicaments to specific areas of their body. For instance, patients who are experiencing severe pain may require pain killers daily or multiple times per day. Absent the use of an implantable pump or the like, a patient of this type would be subjected to one or more painful injections of medication multiple times during the course of the day. In the case of pain associated with more remote areas of the body, such as the spine, these injections may be extremely difficult to administer and particularly painful for the patient. Moreover, attempting to treat conditions like these through oral or intravascular administration of medication often requires higher doses of such medication. This may cause severe side effects. Thus, it is widely recognized that utilizing an implantable pump may be beneficial to both the patient and the treating physicians.

Many implantable pump designs have been proposed, including pumps employing mechanical means for and gas pressure driven propellant means for expelling fluids or active substances from the pump. The present invention is directly related to the latter. More particularly, the apparatus and methods taught in the present application are capable of being utilized with many different types of gas driven pumps, such as those shown in U.S. Pat. Nos. 4,969,873; 5,085,656; 5,336, 194; 5,836,915; 5,722,957; 5,814,019; 5,766,150; and 6,730, 060, as well as U.S. Patent Application Publication Nos. 2006/0259015, 2006/0259016, 2006/0271021, 2006/021022, 2007/0005044, and 2007/0112328, and U.S. patent application Ser. No. 12/069,385. The disclosure of each of the above-noted patents and patent applications are hereby incorporated by reference herein, and certain of these references may be referred to throughout the present application.

Figure 1:
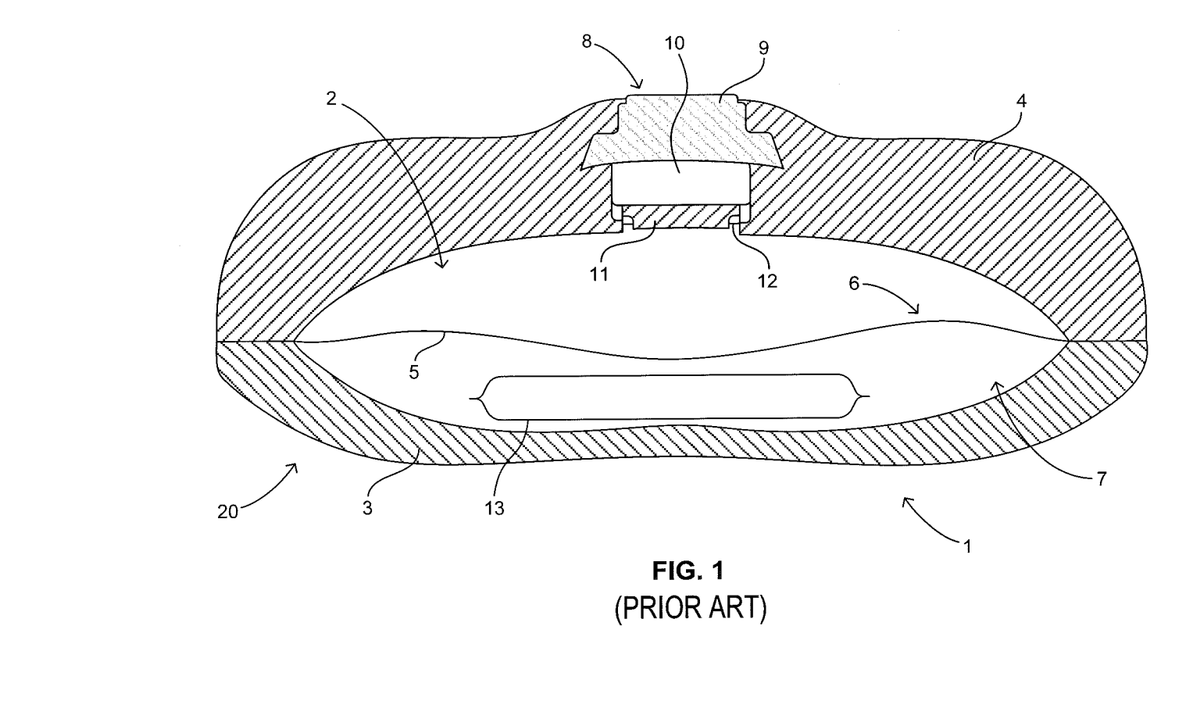
FIG. 1 is a cross-sectional side view of a prior art implantable pump having a propellant pillow disposed within a propellant chamber.
Figure 2:
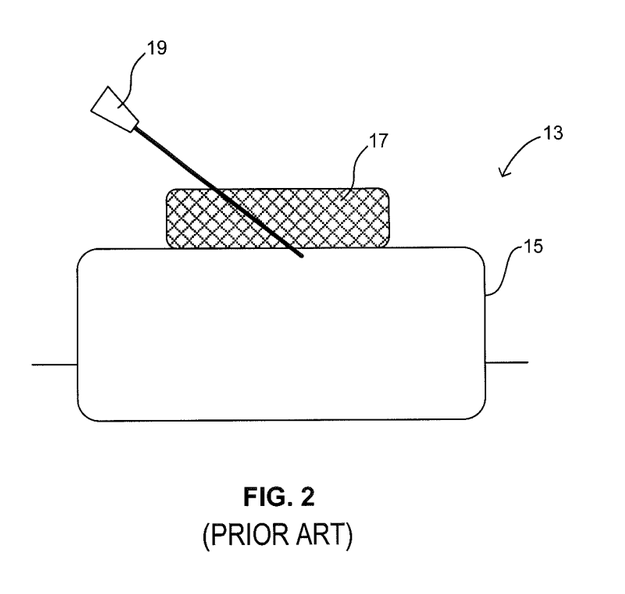
FIG. 2 is an enlarged cross-sectional illustration of the propellant pillow shown in FIG. 1 with a needle inserted therein.

In general, gas driven implantable pumps, like those taught in each of the above-noted patents and patent applications, utilize an expandable propellant (e.g., an isobarically expanding gas) that acts upon a membrane to push medicament or other fluid from the pump. A common problem with such pumps revolves around the filling of the propellant chamber with propellant. Above-noted U.S. Pat. No. 5,766,150 ("the '150 patent") discloses an apparatus and method for use in such a filling process. As is shown in FIG. 1 of the '150 patent (reprinted as FIG. 1 of the present case), that patent teaches the use of a propellant pillow 13, which is filled with a gas propellant and placed into a propellant chamber 7 of an implantable pump. The chamber is thereafter sealed. FIG. 2 shows pillow 13 in greater detail, in particular, the fact that the pillow includes a propellant bag 15 and septum 17 affixed to the bag, which are not labeled as such in the '150 patent. Because bag 15 consists of a material through which the propellant may defuse (i.e., a permeable material), the gas slowly diffuses through the wall of the pillow and into chamber 7. Thus, the use of pillow 13 allows time for the propellant chamber and the remainder of the pump to be assembled before the gas escapes therefrom.

During assembly of a pump in accordance with the methods taught in the '150 patent, the assembly steps first include punching bag 15 from an air padded foil or the like, evacuating it of all gases, and subsequently refilling it with a propellant. These steps generally involve the use of at least one cannula, needle, or syringe 19 that pierces self-sealing silicone septum 17 to both evacuate all gases and introduce propellant. After being filled, pillow 13 is then introduced into a pump that has been divided into propellant chamber 7 and a fluid/medicament storage chamber 6. Subsequent to inserting pillow 13 into propellant chamber 7 of the pump, that chamber is sealed and evacuated of all gases. This allows the propellant to solely permeate through the walls of bag 15 and into propellant chamber 7. This method is generally applicable to any gas pressurized implantable pump, including the ones described in the various prior art references listed above and incorporated by reference herein.

While the device and methods taught in the '150 patent have been utilized for some time in filling implantable pumps such as those disclosed above, they are not without their drawbacks. For instance, the initial evacuation of and subsequent filling of propellant within pillow 15 sometimes results in the structure of the bag being damaged by the syringe(s) 19. More particularly, evacuation of gas from bag 15 (i.e., creating a vacuum) causes the walls of the bag to collapse upon themselves and sometimes into contact with the point of the syringe(s). This may result in the walls being pierced, which thereby leads to a faster escape of the propellant from bag 15 than is desired. Thus, while the '150 patent suggests placing the pillow within a sealed propellant chamber in approximately two minutes, this time period is significantly reduced when the bag walls are damaged. More often than not, this damage to pillow 13 results in less propellant ultimately being contained with the propellant chamber.

Figure 3:
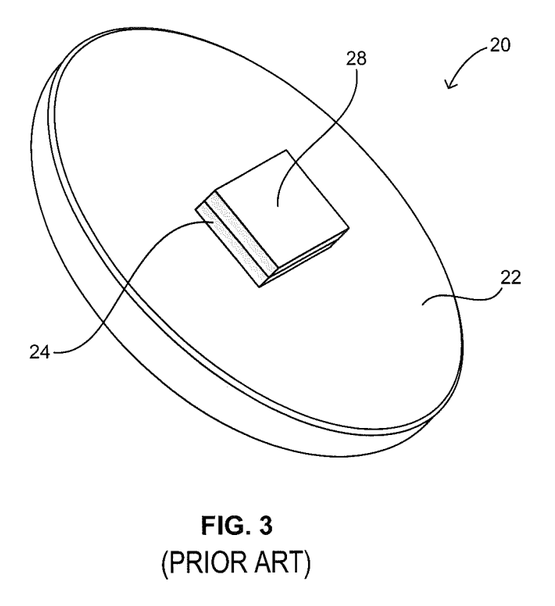
FIG. 3 is a perspective view of a propellant pillow in accordance with another existing propellant pillow design.
Figure 4:
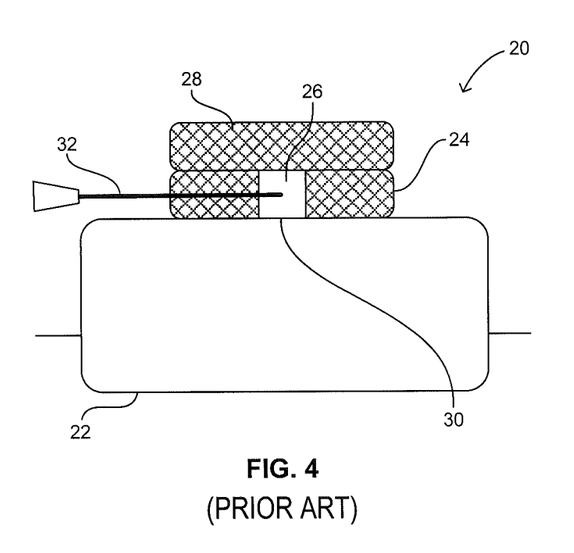
FIG. 4 is a cross-sectional side view of the propellant pillow shown in FIG. 3 with a needle inserted therein.

Above-noted U.S. patent application Ser. No. 12/609,385 ("the '385 Application") discloses a propellant pillow that improves upon the one taught in the '150 patent. As is shown in FIGS. 3 and 7 of the '385 Application (reprinted as FIGS. 3 and 4 of the present case), that application teaches the use of a propellant pillow 20 that includes a propellant bag 22, a first septum 24, including an opening 26, and a second septum 28 overlying the first septum. At least one opening 30 is also preferably created in propellant bag 22. This design allows for a needle or syringe 32 to be inserted laterally through first septum 24 until the tip of the needle extends into opening 26 (best shown in FIG. 4). In this position, the needle can be utilized to evacuate all air or other gas that is contained within propellant bag 22, such that the air or gas exits through opening 30 of propellant bag 22, into opening 26 of first septum 24, and through the needle. Like in the propellant pillow taught in the '150 patent, this evacuation step generally results in propellant bag 22 collapsing upon itself. However, because of the design of propellant pillow 20, needle 32 is not permitted to engage any portion of propellant bag 22 during its collapse. The propellant bag can be filled in a like manner through opening 26 and first septum 24, through opening 30 and propellant bag 22, and into the propellant bag.

Although the above-discussed propellant bags and propellant filling techniques are indeed useful in the filling operation of a propellant bag of an implantable pump, they no doubt require a series of steps that are time consuming and therefore likely to add costs to the manufacture of each individual implantable pump. For instance, the steps required to fill the propellant pillows of the '150 patent and '385 Application require time and effort.

Therefore, there exists a need for an improved manufacturing technique for a propellant pillow for use in filling a propellant chamber of an implantable pump that produces a filled propellant pillow without the need for a separate filling operation.

BRIEF SUMMARY OF THE INVENTION

A first aspect of the present invention is a method of filling an implantable pump with a propellant. In one embodiment of this first aspect, the method includes the steps of filling a cylinder with the propellant, fusing a portion of the tube to create a propellant pillow, inserting the propellant pillow in a propellant chamber of the implantable pump and allowing the propellant to permeate through the propellant pillow.

In other embodiments of the first aspect, the fusing step may create first and second propellant pillows. The inserting step may include inserting the first propellant pillow in a first propellant chamber of a first implantable pump and the second propellant pillow in a second propellant chamber of a second implantable pump. The fusing step may include a high frequency welding process. The method may further include the steps of cooling the cylinder prior to the filling step, warming the cylinder subsequent to the filling step, and evacuating the propellant chamber prior to the allowing step. At least the warming step may accelerate the permeation of propellant into the propellant chamber.

The cylinder may be constructed of polyvinyl chloride, polyurethane, or the like. The fusing step may create three propellant pillows and the inserting step may include inserting the three propellant pillows in three different propellant chambers of three different implantable pumps. The method may further include the steps of fusing first and second ends of the cylinder, wherein the filling step occurs after fusing of the first end and before fusing of the second end.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 7b is a top view of the cylinder shown in FIG. 7a.

DETAILED DESCRIPTION

In describing the preferred embodiments of the subject illustrated and to be described with respect to the drawings, specific terminology will be used for the sake of clarity. However, the invention is not intended to be limited to any specific terms used herein, and it is to be understood that each specific term includes all technical equivalents, which operate in a similar manner to accomplish a similar purpose.

Figure 5:
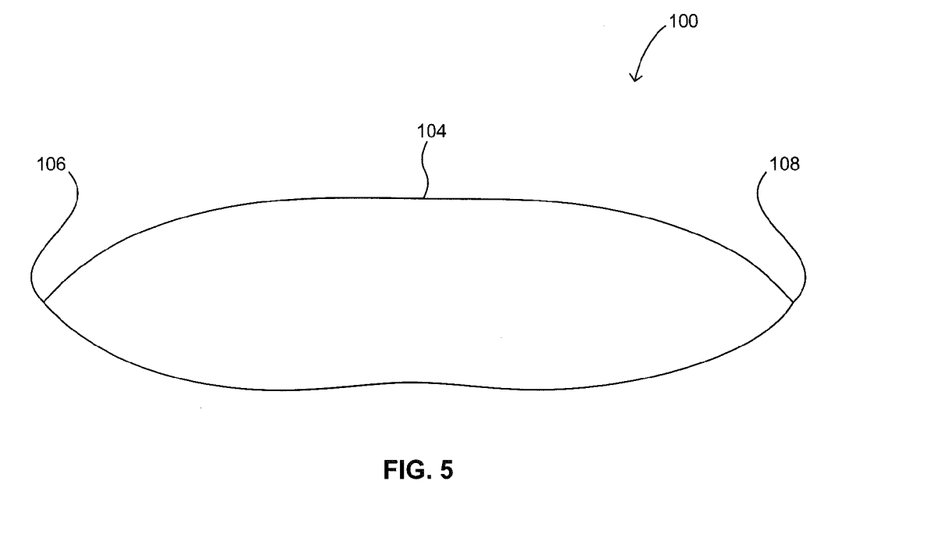
FIG. 5 is a cross-sectional side view of a propellant pillow in accordance with one embodiment of the present invention.

Referring to FIG. 5, there is shown an improved propellant pillow 100 in accordance with the present invention. As is shown in that figure, as well as certain of the figures that follow, propellant pillow 100 is made up of a body 104 that is fused at lines 106 and 108. Although shown as being formed from a single body 104, it is to be understood that pillow 100 could be formed from multiple membranes or the like. Moreover, although shown having an undulating shape, different portions of body 104 can be of any cross-sectional shape including concave or convex. Likewise, although propellant pillow 100 is preferably of a circular shape when viewed from the top, such can be of any shape or size suitable for use in an implantable pump, including oval, square, rectangular, and/or oblong shapes.

Body 104 of propellant pillow 100 may be constructed of any suitable material for containing a propellant utilized in an implantable pump. For instance, as will be discussed more fully below, body 104 is preferably constructed of a dielectric material, such as polyvinyl chloride ("PVC") or polyurethane, so that such material is capable of being welded through the use of a high frequency ("HF") technique. In the case where body 104 is formed from two or more portions, it is preferable to have the portions constructed of the same material. However, the portions could be of different materials, as long as they are capable of being welded together as mentioned above and discussed further below.

Figure 6:
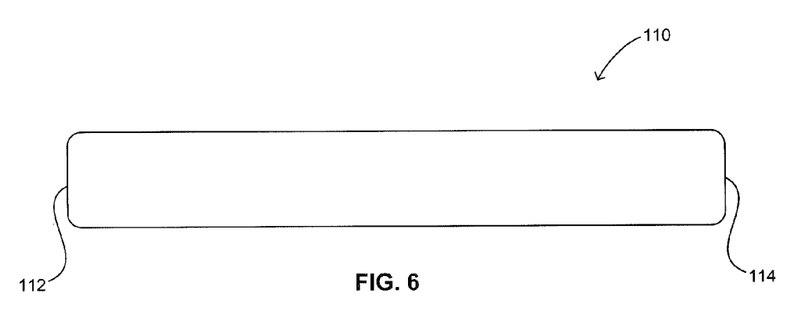
FIG. 6 is a cross-sectional side view of a cylinder utilized in creating a plurality of the propellant pillows shown in FIG. 5.
Figure 7A:
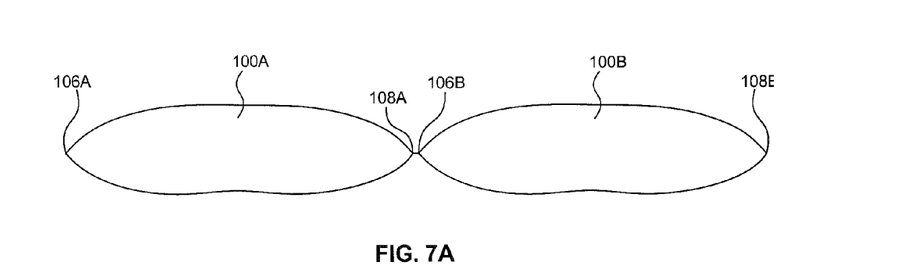
FIG. 7a is a cross-sectional side view of the cylinder shown in FIG. 6 subsequent to two propellant pillows, like that shown in FIG. 5, being formed therefrom.
Figure 7B:
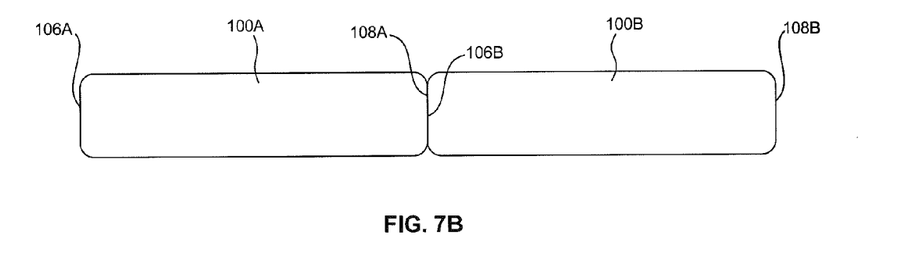

With reference to FIGS. 6 and 7, the method of forming propellant pillow 100 will now be discussed. Specifically, a cylinder 110 is shown in FIG. 6 as being roughly double the size of propellant pillow 100. While shown a sealed at both of its ends, it is to be understood that cylinder 110 can be open at one end or even tubular. Cylinder 110 is formed of the same material as body 104. In the situation where body 104 is formed of a plurality of portions, cylinder 110 may include corresponding portions that may or may not be of the same material. More particularly, where body 104 is solid or the portions of body 104 are to be of the same material, cylinder 110 may be of a uniform material (i.e., of a solid construction). On the other hand, where the portions of body 104 are to be of different materials, cylinder 110 may be formed from separate portions constructed of the respective materials. As noted above, cylinder 110 is shown as approximately double the size of propellant pillow 100, so that it may be utilized to create two chambers. However, cylinder 110 may be larger or smaller than is shown. For instance, cylinder 110 may be sized larger so as to create three or more pillows 100 or smaller so as to create two or more smaller pillows (not shown). Likewise, cylinder 110 may be of any shape, not simply cylindrical.

In a preferred embodiment where cylinder 110 is of a solid construction, the cylinder is preferably first fused at one or both of ends 112 or 114. Cylinder 110 is then cooled filled with a liquid-phase propellant, which is suitable for use in an implantable pump (i.e., expandable), such as any of the implantable pumps taught in the above-discussed references, which are incorporated by reference herein. In preferred embodiments, during the filling process, the propellant is kept in the liquid state because of the cooling of cylinder 110, as opposed to the liquid-vapor state it is generally in when the pump is implanted in the body of a patient. Warming of cylinder 110 will put the propellant into this latter stage. The filling process may be accomplished in many different ways, utilizing many different apparatus. For instance, in a preferred embodiment, a syringe it utilized to inject the liquid phase propellant into cylinder 110. Once filled, cylinder 110 is either ready for the formation of separate pillows (in the case of where both ends 112 and 114 have already been fused) or can be fused at the other of end 112 or 114. The fusion process of ends 112 and 114 can be performed in the same way as is discussed below in connection with the formation of multiple pillows 100. Of course, other possibilities exist, including the original formation of cylinder 110 with a closed end (i.e., cup-shaped).

FIGS. 7a and 7b show cylinder 110 subsequent to formation of two different propellant pillows 100a and 100b. Essentially, cylinder 110 has been fused at its center (or thereabouts) in order to form the two pillows, which are substantially similar to that shown in FIG. 5. Pillow 110a includes end 106a that is essentially end 112 of cylinder 110 and end 108a, while pillow 110b includes end 108b that is essentially end 114 of cylinder 110 and end 106b. Ends 108a and 106b are connected to each other where tube 110 has been fused, and can be cut or otherwise separated in order to produce separate pillows 100a and 100b. Pillows 100a and 100b are thusly formed already filled with a propellant, and are ready for use in an implantable pump. The top view of FIG. 7b illustrates that the fusion occurs along a line of cylinder 110. Of course, in other embodiments, the fusion may occur in any pattern to create differently sized and/or shaped pillows.

In a preferred embodiment, the fusing technique employed in creating pillows 100a and 100b, as well as sealing of ends 112 and 114 of cylinder 110 in certain embodiments, is HF welding. Such a process is also known as dielectric sealing and R.F. (Radio Frequency) heat sealing. This type of procedure, generally requires the use of materials capable of being heated with high frequency electromagnetic waves, for instance, certain polymers having chemical dipoles such as PVC, polyurethane, polyamides and acetates (certain of such discussed above). Essentially, high frequency welding uses this property to soften the polymers for joining. Utilizing the high frequency welding technique allows for only areas of localized heat, which preserves other portions of the materials, and prevents inadvertent destruction or even explosion of the propellant. Thus, such provides for the safe creation of structurally sound chambers 100a and 100b.

In a preferred procedure, a machine offered under the name CompoSeal Modilea by Fresenius Kabi Deutschland GmbH is utilized to create separate chambers 100a and 100b. Cylinder 110 is placed between two dies, which essentially direct the welding process. When the dies are pressed together, high frequency waves (approximately 27.12 MHZ) are passed through the small area between the dies. This high frequency field causes the molecules in the cylinder material to move and get hot (only locally), and the combination of this heat and the pressure provided by the dies causes the weld to take the shape of the die.

While a high frequency welding process is discussed above as being preferred, other processes are contemplated. For instance, cylinder 110 may be heat stamped in accordance with well known methods, ultrasonically welded or fused through the use of a laser. Of course, both of these processes results in the creation of heat, which can be detrimental to both the cylinder materials and the propellant. Thus, employing such processes may require the use of different materials and/or propellants. Moreover, it is contemplated to use an adhesive bond. Again, the materials and/or propellants employed may be dictated by such a process.

Regardless of what fusing technique is utilized, the above-discussed process results in the creation of two or more propellant pillows, while limiting the overall filling steps that are required. This is a significant improvement over the filling processes disclosed in the '150 patent and the '385 Application. However, the remaining steps in filling the propellant chamber of a pump are similar to that taught in those references, i.e., pillow 100 is placed within a propellant chamber during assembly of the pump, the propellant chamber is evacuated and the propellant is allowed to permeate through body 104.

The above-discussed propellant pillow formation manufacturing technique may also be useful in forming propellant chambers for use directly in an implantable pump. In this regard, cylinder 110 would be constructed of materials suitable for use in a propellant chamber, as opposed to in connection with a permeable propellant pillow. After creation of one or more chambers, such can be directly introduced into a pump during an assembly process. This would completely negate the need for other filling processes. In such a case, it is also envisioned to design the propellant chamber in a similar fashion to those disclosed in above-noted U.S. Pat. No. 5,814, 019 ("the '019 patent"). In particular, the '019 patent teaches a propellant chamber that is made up of partitions 6 and P, which are each films comprising a metal foil flanked on each side with a polymer support film. Of course, any other suitable membrane design may be employed, including propellant chambers solely comprising metal foil membranes only covered on one side with a polymer. However, creating such propellant chambers may require metal films to be applied after the initial creation of the chamber.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of filling an implantable pump with a propellant comprising the steps of:
   filling a permeable cylinder with the propellant;
   fusing only a portion of the already filled cylinder to create a propellant pillow;
   inserting the propellant pillow in a propellant chamber of the implantable pump; and
   allowing the propellant to permeate through the propellant pillow.

2. The method of claim 1, wherein the fusing step creates first and second propellant pillows.

3. The method of claim 2, wherein the inserting step including inserting the first propellant pillow in a first propellant chamber of a first implantable pump and the second propellant pillow in a second propellant chamber of a second implantable pump.

4. The method of claim 1, wherein the fusing step includes a high frequency welding process.

5. The method of claim 4, wherein the cylinder is constructed of polyvinyl chloride.

6. The method of claim 4, wherein the cylinder is constructed of polyurethane.

7. The method of claim 1, wherein the fusing step creates three propellant pillows and the inserting step including inserting the three propellant pillows in three different propellant chambers of three different implantable pumps.

8. The method of claim 1, further comprising the steps of fusing first and second ends of the cylinder, wherein the filling step occurs after fusing of the first end and before fusing of the second end.

9. The method of claim 8, wherein the fusing step includes a high frequency welding process.

10. The method of claim 9, wherein the cylinder is constructed of polyvinyl chloride.

11. The method of claim 9, wherein the cylinder is constructed of polyurethane.

12. The method of claim 8, wherein the fusing step creates first and second propellant pillows.

13. The method of claim 12, wherein the inserting step includes inserting the first propellant pillow in a first propellant chamber of a first implantable pump and the second propellant chamber in a second propellant chamber of a second implantable pump.

14. The method of claim 1, further comprising the step of cooling the cylinder prior to the filling step.

15. The method of claim 14, further comprising the step of warming the cylinder subsequent to the filling step.

16. The method of claim 1, further comprising the step of evacuating the propellant chamber prior to the allowing step.

* * * * *